(12) United States Patent
Mahoney

(10) Patent No.: US 9,194,857 B2
(45) Date of Patent: Nov. 24, 2015

(54) SEALING APPARATUS FOR ELECTRICAL APPARATUS OIL SAMPLER AND CONDITIONER FOR SOLID STATE SENSORS

(71) Applicant: BPL Global, Ltd., Cranberry Township, PA (US)

(72) Inventor: Steven Mahoney, Beaverton, OR (US)

(73) Assignee: Serveron Corporation, Beaverton, OR (US)

( * ) Notice: Subject to any disclaimer, the term of this patent is extended or adjusted under 35 U.S.C. 154(b) by 331 days.

(21) Appl. No.: 13/889,381

(22) Filed: May 8, 2013

(65) Prior Publication Data

US 2013/0319078 A1 Dec. 5, 2013

Related U.S. Application Data

(60) Provisional application No. 61/654,984, filed on Jun. 4, 2012.

(51) Int. Cl.
*G01N 33/28* (2006.01)
*H01F 27/12* (2006.01)
*H01F 27/40* (2006.01)

(52) U.S. Cl.
CPC ............... *G01N 33/28* (2013.01); *H01F 27/12* (2013.01); *H01F 27/402* (2013.01); *H01F 2027/404* (2013.01); *Y10T 29/49002* (2015.01)

(58) Field of Classification Search
CPC ................ G01N 33/2841; H01F 2027/404
USPC ........................................... 73/19.11
See application file for complete search history.

(56) References Cited

U.S. PATENT DOCUMENTS

| | | |
|---|---|---|
| 4,112,737 A | 9/1978 | Morgan |
| 5,279,795 A | 1/1994 | Hughes et al. |
| 5,659,126 A | 8/1997 | Farber |
| 6,365,105 B1 | 4/2002 | Waters et al. |
| 6,391,096 B1 | 5/2002 | Waters et al. |
| 7,249,490 B2 | 7/2007 | Pendergrass |
| 7,667,461 B2 | 2/2010 | Trygstad et al. |
| 8,748,165 B2 | 6/2014 | Vangbo et al. |
| 2005/0086998 A1* | 4/2005 | Qin .................... B01D 19/0031 73/31.07 |
| 2005/0121323 A1 | 6/2005 | Hartl et al. |
| 2006/0032742 A1* | 2/2006 | Babes-Dornea ... G01N 27/4045 204/400 |
| 2011/0175623 A1* | 7/2011 | Shrinet .............. G01N 33/2841 324/537 |
| 2012/0123738 A1 | 5/2012 | Dorr et al. |

FOREIGN PATENT DOCUMENTS

CN 1749720 B 12/2010
CN 102359675 A 2/2012

OTHER PUBLICATIONS

First Office action issued by the State Intellectual Property Office of the People's Republic of China in Chinese Patent Application No. 201310219034.5, which is a counterpart to this application; Nov. 18, 2014.

* cited by examiner

*Primary Examiner* — Daniel S Larkin
*Assistant Examiner* — Irving A Campbell
(74) *Attorney, Agent, or Firm* — Hancock Hughey LLP

(57) ABSTRACT

A gas monitoring apparatus and system that provides for reliable and accurate monitoring of gaseous hydrogen and other compounds in dielectric oil. The apparatus provides an environment for and is used in conjunction with metal oxide semiconductor sensors. Apparatus for creating a fluid-tight environment for the metal oxide semiconductor and a heating manifold are detailed.

9 Claims, 13 Drawing Sheets

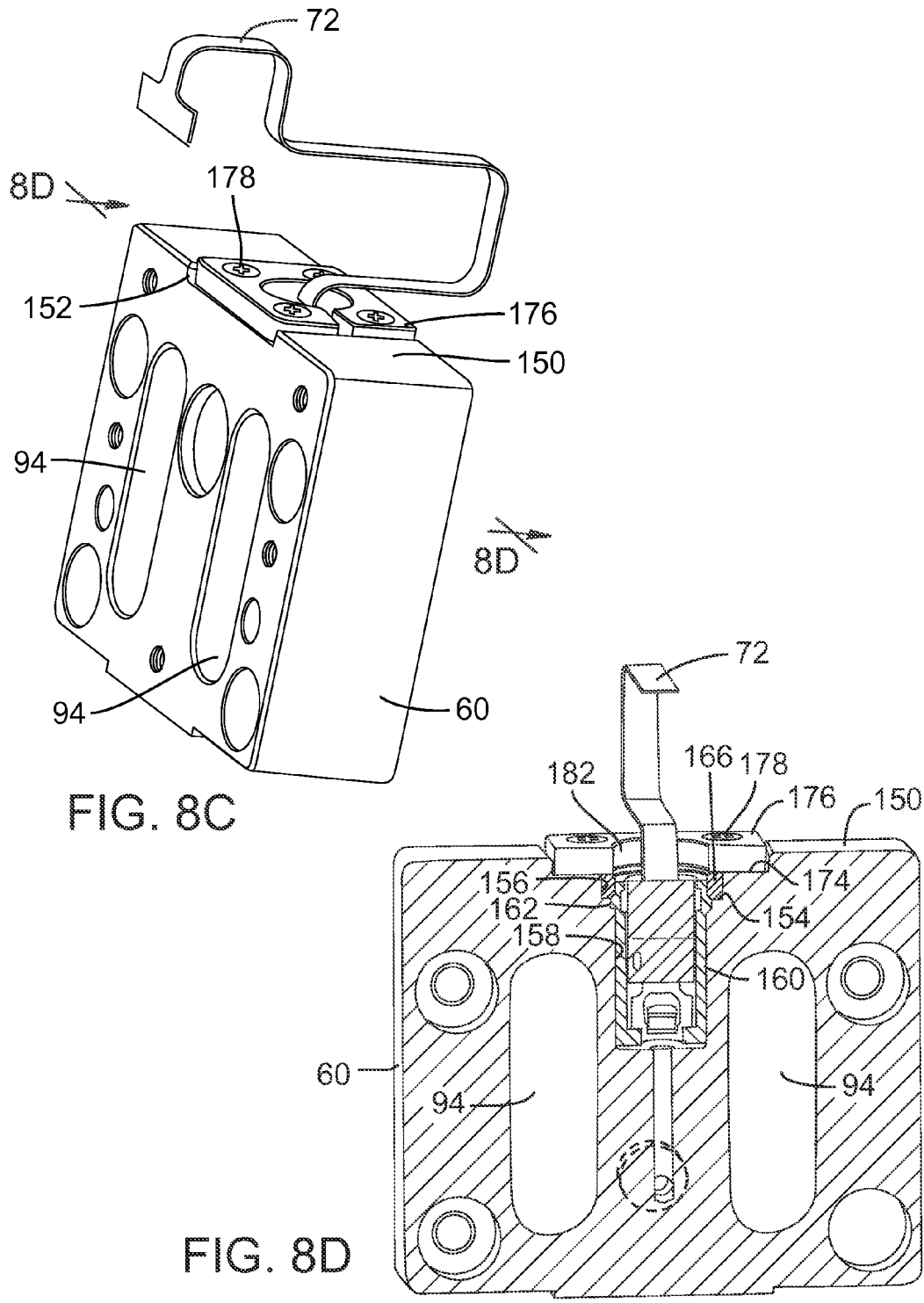

SEALING APPARATUS FOR ELECTRICAL APPARATUS OIL SAMPLER AND CONDITIONER FOR SOLID STATE SENSORS

FIELD OF THE INVENTION

The present invention relates to apparatus and methods for monitoring dissolved gases in liquid, and more particularly, the invention relates to an apparatus and method for sampling and conditioning electrical insulating oils so that gas dissolved in the insulating oils may be monitored reliably by solid state sensors.

BACKGROUND OF THE INVENTION

The electric power industry has for many years recognized that thermal decomposition of the oil and other insulating materials within oil-insulated electrical apparatus can lead to the generation of a number of "fault gases." These phenomena occur in assets such as oil filled transformers (both conservator and gas-blanketed types), load tap changers, transformer windings, bushings and the like. The presence of fault gases may be a measure of the condition of the equipment. As such, detection of the presence of specific fault gases in electrical apparatus, and quantification of those gases can be an important part of a preventative maintenance program.

The presence of fault gases in oil-blanketed transformers with conservators and other utility assets has well documented implications relating to the performance and operating safety of the transformer. There is a substantial body of knowledge available correlating the presence of gases with certain, identified transformer conditions and faults. It is therefore beneficial to monitor the condition of dielectric fluids in electric equipment as a means to maximize performance, and at the same time minimize wear and tear on the equipment, and to thereby minimize maintenance costs and down time. Thus, information relating to the presence or absence of certain fault gases in transformer oil can lead to greatly increased efficiency in the operation of the transformer.

As an example, it is known that the presence of certain fault gases in transformer oil can be indicative of transformer malfunctions, such as arcing, partial or coronal discharge. These conditions can cause mineral transformer oils to decompose generating relatively large quantities of low molecular weight hydrocarbons such as methane, in addition to some higher molecular weight gases such as ethylene and acetylene, and also hydrogen. Such compounds are highly volatile, and in some instances they may accumulate in a transformer under relatively high pressure. This is a recipe for disaster. Left undetected or uncorrected, equipment faults can lead to an increased rate of degradation, and even to catastrophic explosion of the transformer. Transformer failure is a significantly expensive event for an electric utility, not only in terms of down time and the costs of replacement equipment, but also in terms of the costs associated with lost power transmission and dangers to workers and others. On the other hand, by closely monitoring dissolved gases in transformer oil, the most efficient operating conditions for a given transformer can be actively monitored and the transformer load may be run at or near its optimum peak. Moreover, when dangerous operating conditions are detected the transformer can be taken off line for maintenance.

Despite the known need for reliable equipment to monitor gas in oil, designing equipment that holds up to the rigors of on-site conditions has been problematic for a variety of reasons. That said, there are a number of solutions known in the art. For example, mechanical/vacuum and membrane extraction methods and apparatus for degassing transformer oil are well known, as exemplified by U.S. Pat. No. 5,659,126. This patent discloses a method of sampling headspace gas in an electrical transformer, analyzing such gases according to a temperature and pressure dependent gas partition function, and based on the derived analysis predicting specific transformer faults.

An example of a gas extraction apparatus that relies upon a membrane tube for extraction of gas from transformer oil is disclosed in U.S. Pat. No. 4,112,737. This patent depicts a plurality of hollow membrane fibers, which are inserted directly into transformer oil in the transformer housing. The material used for the membrane is impermeable to oil, but gases dissolved in the oil permeate through the membrane into the hollow interior of the fibers. A portable analytical device such as a gas chromatograph is temporarily connected to the probe so that the test sample is swept from the extraction probe into the analytical device for analysis.

Although these devices have provided benefits, there are numerous practical problems remaining to the development of reliable apparatus for extraction, monitoring and analysis of fault gases in transformer oils. Many of these problems relate to the design of reliable fluid routing systems that are redundant enough to provide a relatively maintenance free unit. Since transformers are often located in exceedingly harsh environmental conditions, fluid routing problems are magnified. This is especially true given that the instruments needed to reliably analyze the gases are complex analytical instruments. Two patents that describe the difficulties of these engineering challenges are U.S. Pat. Nos. 6,391,096 and 6,365,105, which are owned by the assignee of this invention and both of which are incorporated herein by this reference. These two patents illustrate not only the complexities of the fluid routing systems needed, but solutions that have proved very reliable. Moreover, many of the existing analytical devices rely upon consumables such as compressed gasses, which increase the costs and makes such devices suitable only for the largest and most expensive utility assets.

One of the most critical points in the analytical process is the extraction apparatus, where gas is actually separated from the electrical insulating oil. While there are several known apparatus for accomplishing this task, experience has shown that the extractor is one point where failure can occur. Stated another way, extraction devices to date have been more fragile than desired and cannot fully withstand the extreme conditions that are routinely encountered in field applications. As a result, additional support equipment or operation constraints are added to compensate for the performance shortcomings and to protect the extraction technology, which adds considerably to the cost. Despite advances in the technological solutions surrounding the extraction devices, especially those described in the '096 and '105 patents, there is a need for an extractor that is reliable and performs accurately under all conditions for substantial lengths of time without being monitored.

Gas sensors such as chromatography and photo-acoustic spectroscopy that are commonly used to analyze extracted gases are very complicated, expensive and as such are typically reserved for monitoring large transformers were multiple gas analysis is cost effective in protecting expensive assets.

For smaller transformers, simpler, lower cost, single gas sensors may be appropriate and sensors such as those described in U.S. Pat. Nos. 5,279,795 and 7,249,490 which are incorporated herein by this reference, utilize a solid state sensor made from palladium-nickel. The problem with these sensors is that they are very susceptible to oil and ambient temperature variations and oil flow. In addition these monitors do not have pumps to actively transport the oil sample over the sensor element. They rely on thermal cycling or diffusion, which greatly slows their response time.

SUMMARY OF THE INVENTION

The advantages of the present invention are achieved in a first preferred and illustrated embodiment of a gas monitoring apparatus and system that provides for reliable and accurate monitoring of gaseous hydrogen and other compounds in dielectric oil. The apparatus provides an environment for and is used in conjunction with a hydrogen sensor assembly such as the metal oxide semiconductor sensors described in U.S. Pat. Nos. 5,279,795 and 7,249,490. The invention provides an environment in which variations in oil temperature and ambient temperature are eliminated and to thereby insure that analytical data are not affected by these environmental conditions. The invention further provides an environment in which variations in changes in oil flow over the sensor element are eliminated in order to eliminate data irregularities that are caused by oil flow dependencies. The invention provides improved response time for obtaining data from the sensor because oil is actively moved over the sensor element. The present invention also incorporates a calibration cycle during which the sensor element is calibrated.

BRIEF DESCRIPTION OF THE DRAWINGS

The invention will be better understood and its numerous objects and advantages will be apparent by reference to the following detailed description of the invention when taken in conjunction with the following drawings.

In FIGS. 8A through 8D the heater manifold and sensor assembly are shown in isolation without adjacent components.

FIG. 8B is a cross sectional view of the exploded heater manifold and sensor assembly shown in FIG. 8A taken along the line 8B-8B of FIG. 8A.

FIG. 8C is a perspective view of the alternative embodiment of the assembled heater manifold and sensor assembly shown in FIGS. 8A and 8B, illustrating the components in an assembled condition.

FIG. 8D is a cross sectional view of the assembled heater manifold and sensor assembly shown in FIG. 8C taken along the line 8D-8D of FIG. 8C.

DETAILED DESCRIPTION OF PREFERRED AND ILLUSTRATED EMBODIMENTS
STRUCTURE

Figure 1:
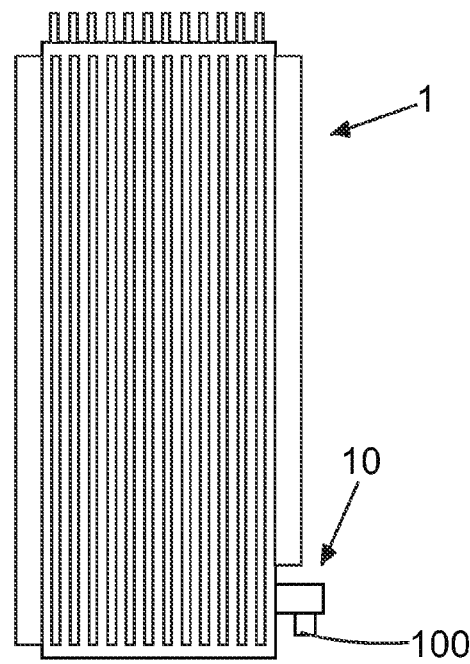
FIG. 1 is a schematic perspective view of an illustrated embodiment of the present invention attached to an oil-filled transformer asset.

With reference to FIG. 1, apparatus and system 10 is illustrated schematically attached to an oil-drain port of an oil-filled electrical device (referred to at times as an "asset"), identified with reference number 1. It will be appreciated that the invention described herein may be used with many different types of electrical devices, and also that the device may be attached to many different locations on the devices. The figures included herein are thus intended to be exemplary but not limiting.

As detailed below, the system and apparatus 10 is comprised of a gas sensing element with associated electronics and cabling, a fluid delivery system to provide fresh samples to the gas sensing element, a thermal control system for the sample fluid, a second thermal control system for the gas sensing element electronics environment, and additional electronics for data logging, communications, power conditioning and alarming.

The apparatus 10 is intended for use on oil filled electrical utility assets such as transformers and load tap changers. As noted above and as shown in FIG. 1, the apparatus 10 is mounted on the utility asset at a valve that accesses the insulating oil within the asset, typically a mineral or ester oil. The system detects trace dissolved hydrogen in the mineral oil and when either a fixed concentration threshold or a rate of change in the hydrogen concentration are exceeded, the system alarms to alert the utility of the hydrogen generation event. As hydrogen is generated in most transformer fault conditions, it is an excellent indicator of a developing fault within the transformer.

Generally described, the apparatus and system 10 functions by drawing a fresh oil sample into a small internal volume containing the gas sensing element. The oil sample is thermally conditioned to a pre-set temperature. When the desired temperature of the sample is achieved, the gas sensing element makes a measurement which is logged within the system. The gas sensing element and its associated electronics are very thermally sensitive. By controlling the thermal environments of these components, the precision, accuracy and reproducibility of the hydrogen readings are greatly improved due to the diminishment of the interferences from differences in temperature reading to reading, and drift is minimized or eliminated.

Additionally, the apparatus and system 10 has a unique capability for calibration. The fluid sample path can be optionally split so that there are two possible sample supplies separated through 3-way valves on the oil inlet and outlet. Both sample paths would be connected to the common oil paths to and from the utility asset. The primary fluid path would deliver oil from the utility asset for standard analysis. The secondary sample path would have an incorporated membrane located between the 3-way sample selection valves. A compressed gas standard could be applied to the gas side of the membrane, which would inoculate and equilibrate with the isolated oil in the secondary sample path. When system calibration is necessary, the secondary sample path would be activated so that the inoculated oil would be introduced into the sensor environment. Excess inoculated oil would be flushed back to the utility asset with fresh oil from the utility asset replenishing the secondary sample path for isolated inoculation. The gas on the gas side of the membrane on the secondary sample path could also be atmospheric air. This would effectively generate a "zero" gas standard devoid of the gas of interest.

Turning now to FIGS. 2 through 10, the basic components of the apparatus and system 10 will be described. Apparatus and system 10 includes three primary sections or systems, each of which comprises multiple components and each of which is detailed herein: an electrical oil cooling and transport pump section 14, a thermal conditioning section 30, and a control system 100.

Figure 2:
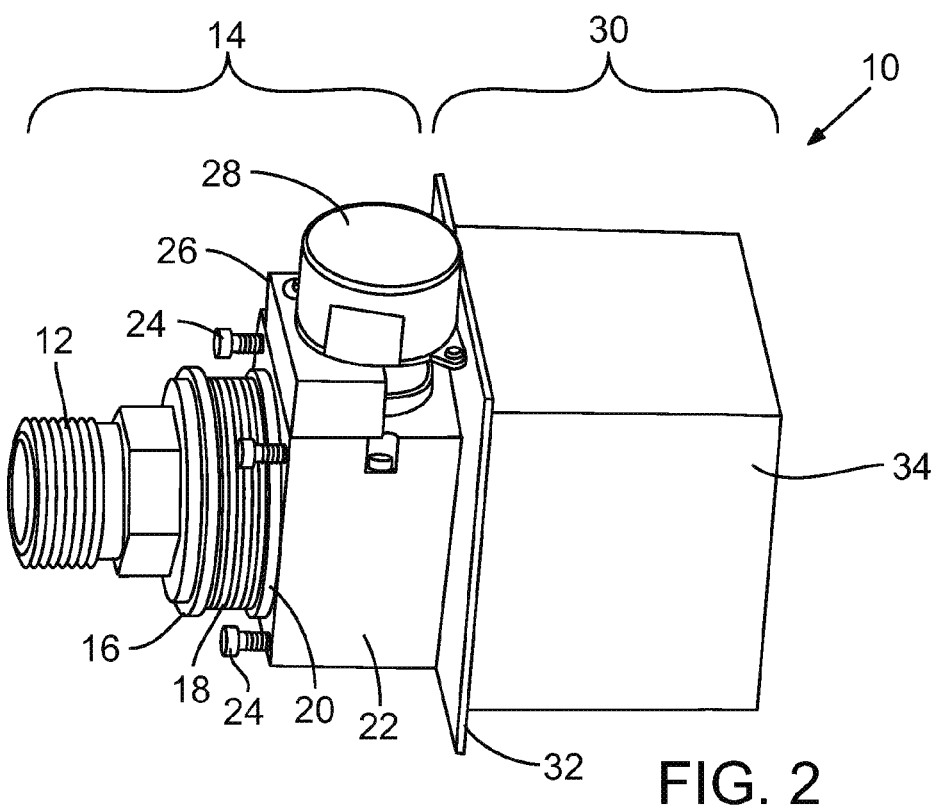
FIG. 2 is a perspective view of one embodiment of the apparatus of the present invention shown in isolation and enclosed in a protective housing.

With reference to FIG. 2, apparatus 10 includes a threaded adaptor 12 that connects to a threaded port in the electrical asset 1 and which is adapted to receive electrical oil from the asset. An electrical oil cooling and transport pump section is shown generally with reference number 14. The cooling and transport pump section 14 includes a first insulation plate 16, a heat sink 18, a second insulation plate 20, all of which are attached to a cold manifold housing 22 with appropriate fasteners such as screws 24. A motor mount 26 is mounted at a top end of the manifold housing 22 and serves as the mount for a stepper motor 28. Heat sink 18 defines a passive cooling manifold that helps to withdraw heat from the fluid from asset 1.

A thermally controlled heating section, identified generally with reference number 30 is mounted to the electrical oil cooling and transport pump section 14. Within the multiple components contained in the thermal conditioning section are individual systems, such as thermal control apparatus 61, which itself comprises multiple individual components and systems including a first thermal zone 65 and a second thermal zone 67, all of which are detailed below. The thermal conditioning section 30 includes an external housing 34 that encloses the components described below. The entire apparatus 10 includes appropriate gaskets and seals to insure a fluid-tight environment.

The optimal performance (consistent precision, accuracy and reproducibility with lowest drift) and life of the sensor assembly 70 is achieved by operating the sensor assembly and its associated analog electronics isothermally, but at two different temperatures. This requires the implementation of first and second distinct and separate thermally controlled zones for the sensor and analog electronics—first and second thermal zones 65 and 67. The first thermally controlled zone 65 is operable to control the thermal conditions associated with the sensor assembly 70; the second thermally controlled zone 67 is operable to control the thermal conditions associated with the analog electronics that control and operate with the sensor assembly 70. Each of the thermally controlled zones 65 and 67 is independently controllable for "heating" and separately for "cooling", as conditions dictate, and each is thermally isolated from the other and from other components of the apparatus 10 and from the ambient environment.

Additionally, the optimal control temperatures for the sensor assembly 70 and the analog electronics are at or below the maximum operating oil and ambient temperatures required for the system 10 based upon the sensor assembly 70 technology. As such, in addition to first and second pulse width modulated heater controls, system 10 incorporates two pulse width modulation controlled Peltier thermoelectric coolers (TEC) to provide continued thermal control at the highest and lowest environmental exposure requirements. The thermoelectric coolers are used to cool the sensor and analog electronic zones for high environmental temperature exposures. For low environmental temperature exposures, the current applied to the thermoelectric coolers is reversed to apply a heating assist to the heater control systems for each of the thermal zones. Therefore, as described in detail below, system 10 utilizes two thermally controlled zones with a total of six thermal control systems, two heater controls, two cooler controls and two controls for operating the TECs in the reverse direction as heater assists.

Figure 3:
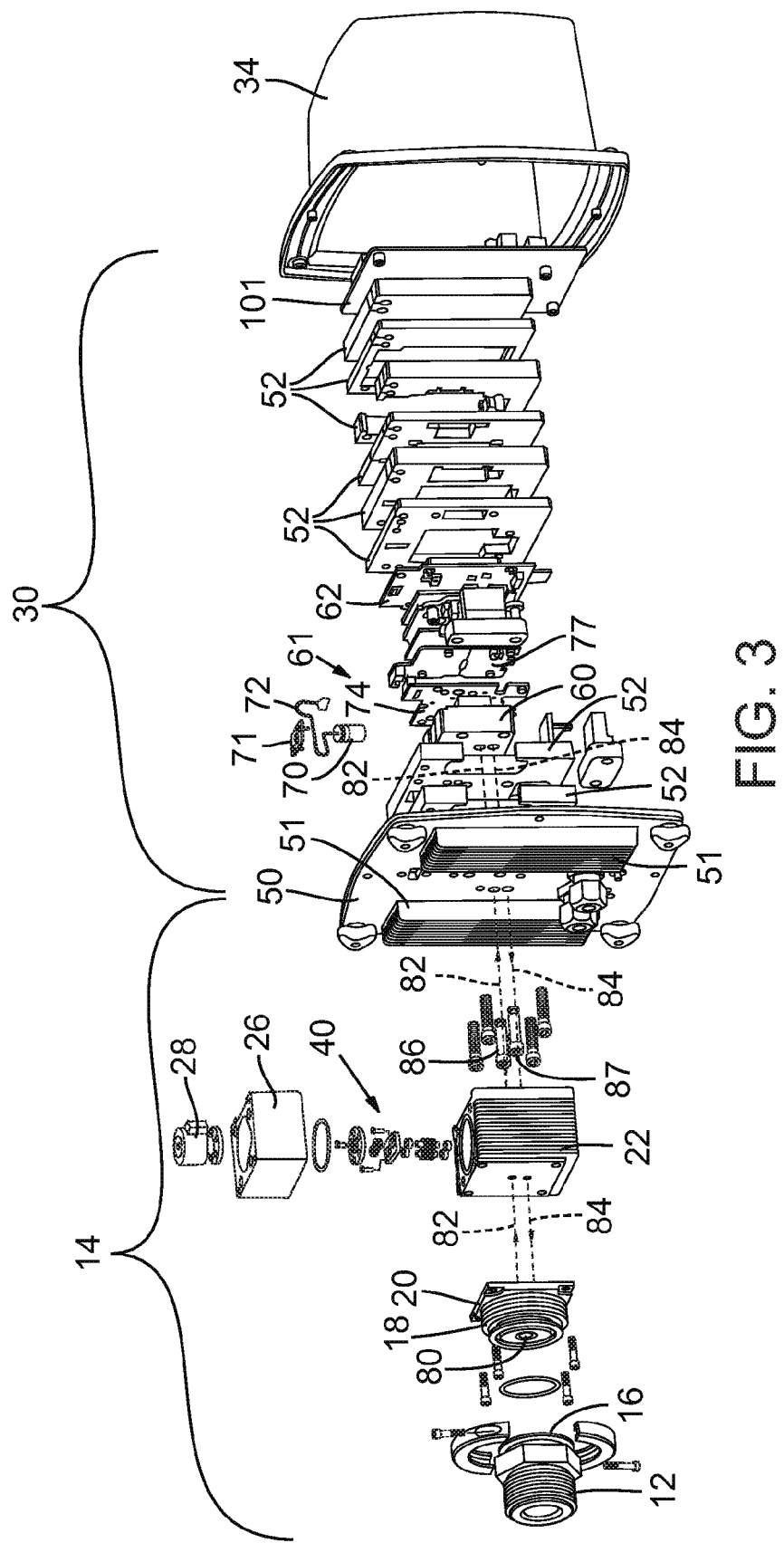
FIG. 3 is perspective and exploded view of the apparatus shown in FIG. 2, illustrating the individual components.
Figure 4:
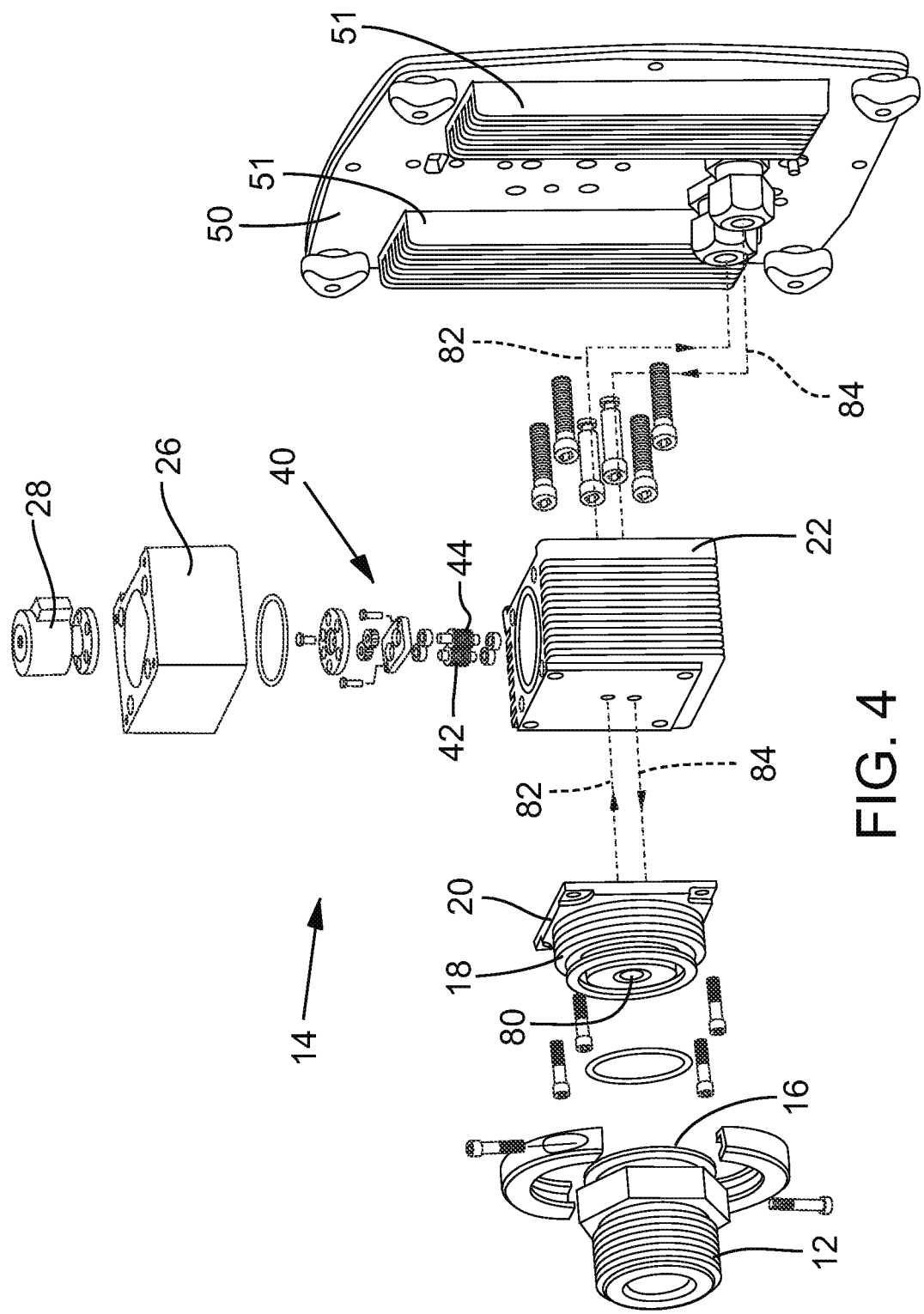
FIG. 4 is a perspective and exploded view of selected components of the apparatus shown in FIG. 3, and specifically, the components of the oil pump and oil cooling section of the apparatus.
Figure 5:
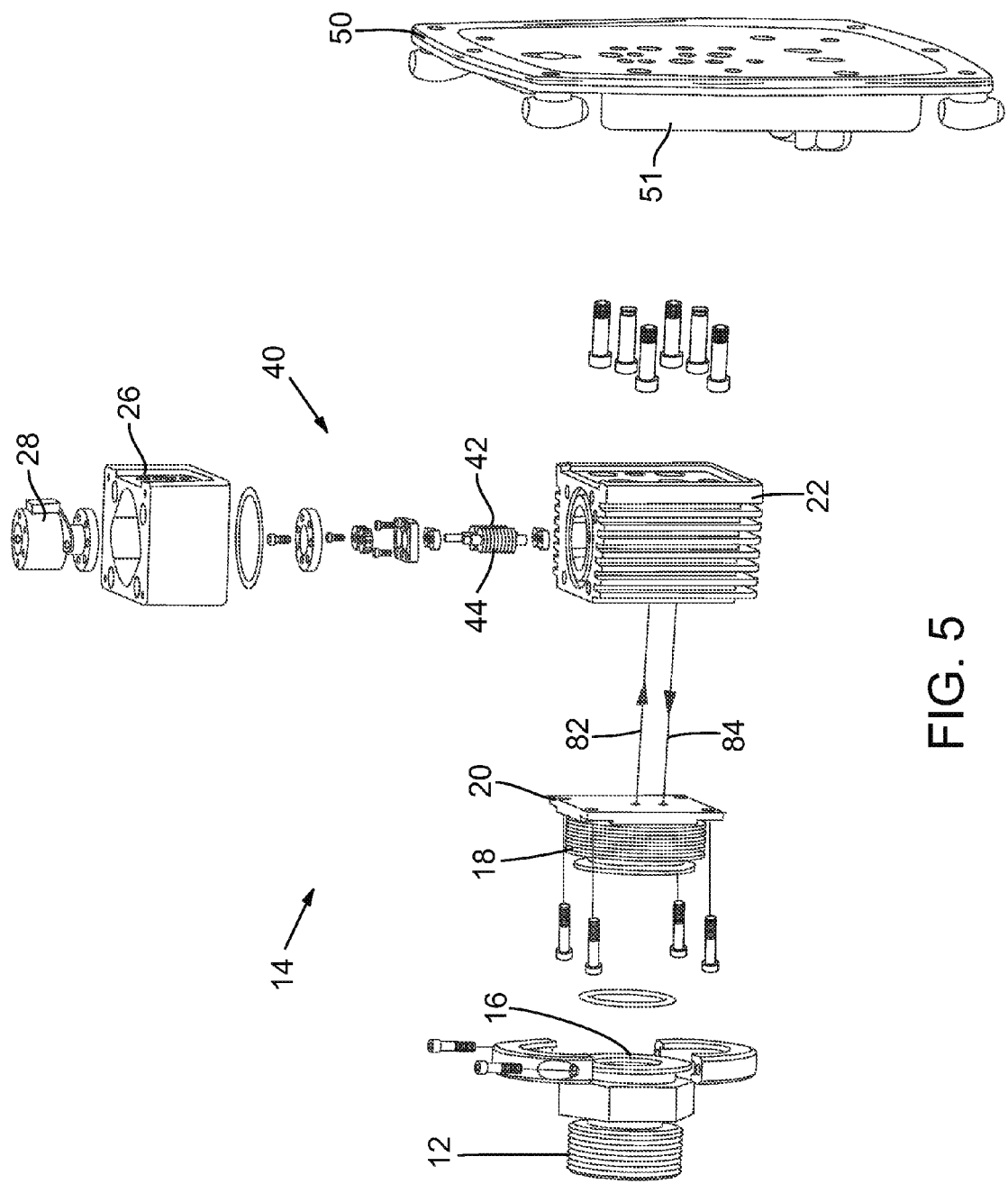
FIG. 5 is a perspective and exploded view of the components of the oil pump and oil cooling section shown in FIG. 4, taken from a different point of view relative to FIG. 4.

The entire apparatus and system 10 including the electrical oil cooling and transport pump section 14 and thermal conditioning section 30 is shown in exploded view in FIG. 3. Electrical oil cooling and transport pump section 14 includes a worm gear drive assembly 40 that is driven by stepper motor 28 and which is configured for precisely controlling flow of fluid through apparatus 10. Although not described in great detail, but as shown in FIGS. 4 and 5, worm drive gear assembly 40 includes appropriate gearing and sealing components to insure a fluid-tight and leak-free environment and defines a precisely controllable metering pump for controlling flow of oil through apparatus 10. As detailed below, apparatus 10 includes porting that defines fluid flow paths of aliquots of oil from the reservoir of oil in asset 1 through the apparatus 10, specifically, from asset 1 into electrical oil cooling and transport pump section 14, then into thermal conditioning section 30, and more specifically, sensor 70, and back to asset 1.

Returning to FIG. 3, the fluid sample flow path is shown schematically. Specifically, cooling heat sink 18 is mounted to adaptor 16 and includes a sample core tube 80 that defines an inlet for fluid from asset 1, and as described below, functions as a cooling chamber for oil received from asset 1. An oil inlet path 82 defines fluid flow routing into cold manifold housing 22, and as more specifically described below, into the worm gear chamber within the housing 22. The oil inlet path continues from housing 22 through appropriate porting such as insulating tubes 86 and 87 to heater manifold 60, and as more specifically described below, into a chamber in the heater manifold that houses sensor assembly 70. An oil return path 84 is defined by appropriate porting from the chamber in the heater manifold 60, through cold manifold housing 22, and back into asset 1. In order to maintain thermal isolation of oil, insulating tubes 86 and 87 are preferably nylon because of its thermal efficiency and because it minimizes transfer of heat from the tubing to surrounding components.

Figure 6:
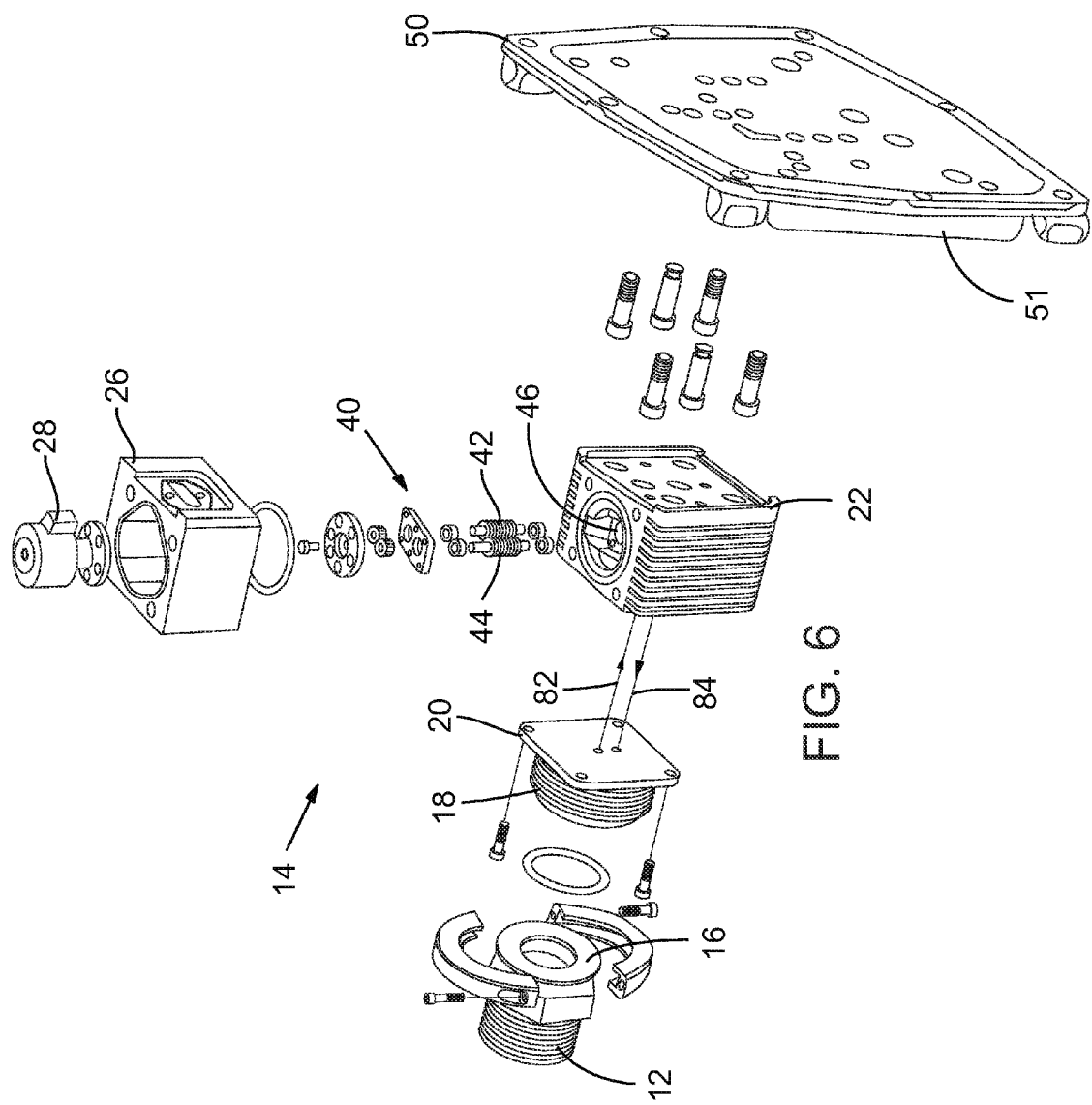
FIG. 6 is a yet another perspective and exploded view of the oil pump and oil cooling section of the apparatus shown in FIG. 3 from yet another point of view.

The cold manifold housing 22 is shown in isolation in FIG. 6. Worm drive gear assembly 40 includes a pair of worm gears 42 and 44 with opposite spiral windings that are driven by stepper motor 28 and which are housed in a worm gear chamber 46 in the manifold housing 22. When worm gears 42 and 44 are in the operable positions in cold manifold housing 22, the opposed spiral windings intermesh to define a portion of the oil flow path over the intermeshed windings. Oil inlet path 82 leads into worm gear chamber 46 and operation of worm gears 42 and 44 by stepper motor 28 causes controlled and known volumes of fluid to flow through the inlet path into heater manifold 60.

Beginning with the components immediately adjacent electrical oil cooling and transport pump section 14, thermal conditioning section 30 includes a plate 50 between gasket 32 and the cold manifold housing 22. Plate 50 is a metallic plate that serves as a supporting structure for components of electrical oil cooling and transport pump section 14 and thermal conditioning section 30, and for purposes of this description of the invention, effectively separates the cooling side from the hot side. Plate 50 includes a pair of heat sinks 51 attached to the plate on the side of the plate that faces electrical oil cooling and transport pump section 14. Plural insulating blocks 52 are incorporated in the heating section in order to thermally insulate and isolate a heater manifold 60, which is a relatively massive, preferably monolithic block of a metal such as aluminum that has excellent heat transfer properties, and which is heated with resistive heating elements that are attached to a printed circuit board 74 that is a component of the thermal control assembly 61. The insulating blocks are preferably urethane foam, but numerous materials may be utilized for the thermal insulation properties. Heater manifold 60 has an internal chamber 90 (FIG. 7) that houses the sensor assembly 70 and the sensor assembly is retained in the chamber 90 with a bracket 71 that threads into bores in the manifold 60. Sensor assembly 70 includes the electronics that define the gas sensors, and will be understood to be of the type described in U.S. Pat. Nos. 5,279,795 and 7,249,490. The sensor assembly 70 is electrically connected to circuit board 62 with a flex circuit 72.

Thermal conditioning section 30 comprises four separate printed circuit boards, each of which contains operational firmware and electronics for control of apparatus 10 and for facilitating networked communications capabilities for the apparatus and system, and all of which comprise control system 100. With reference to the figures, the four circuit boards are identified as first heater board 74, second heater board 77, analog sensor board 62 and main control board 101. Critical functions of each are detailed below.

Both of the first and second thermally controlled zones are located in the thermal control assembly shown generally with reference number 61.

Figure 7:
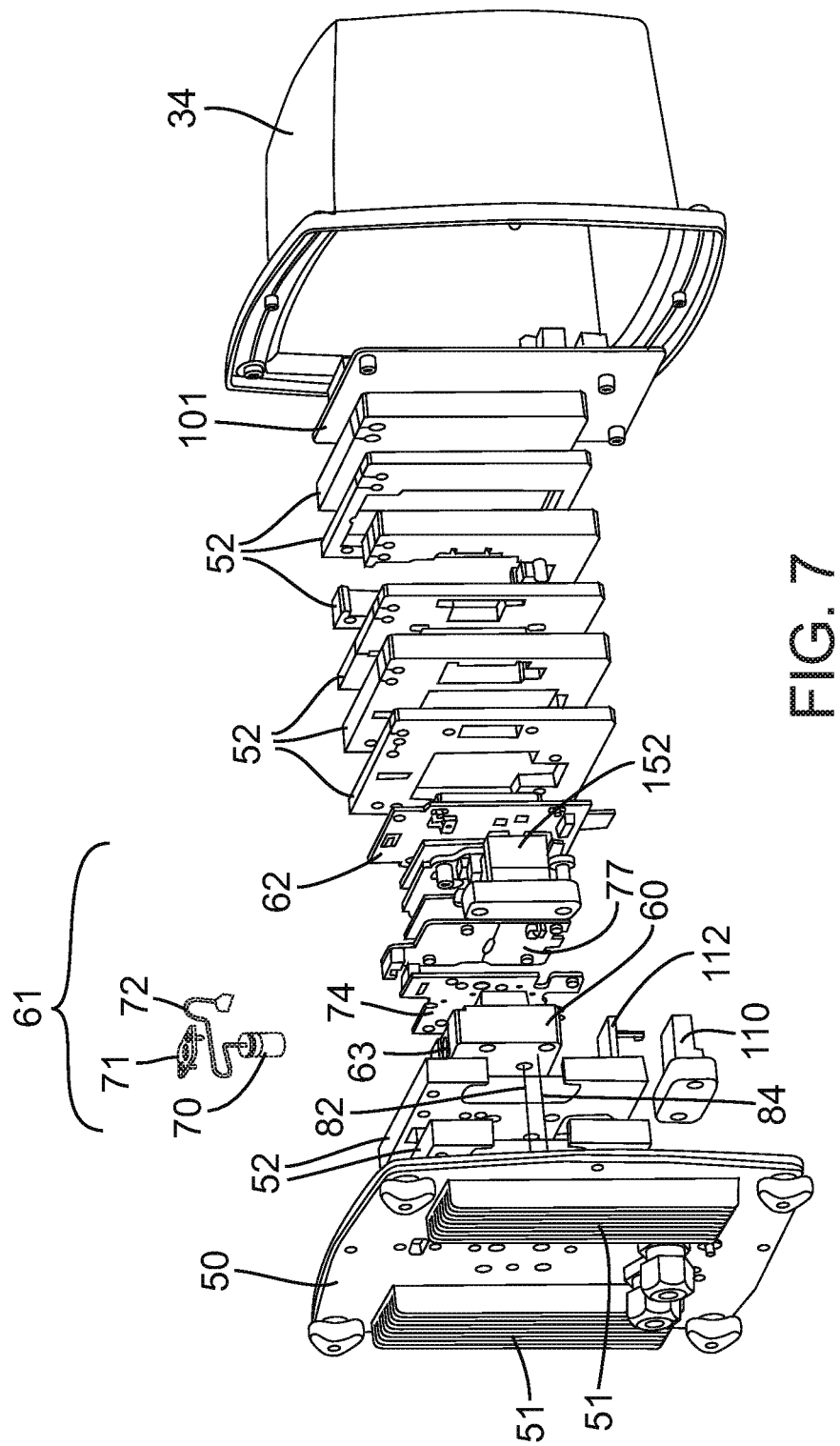
FIG. 7 is a perspective and exploded view of selected components of the thermal conditioning section of the apparatus shown in FIG. 3.

As shown in the exploded view of FIG. 7, the components of the thermal conditioning section 30 are sandwiched together and when assembled are retained in the housing 34. The plural insulating blocks 52 define an insulation barrier that entirely surrounds the components of the thermal control assembly 61 and effectively thermally isolates all components of the assembly. Beginning on the left hand side of FIG. 7 and generally moving toward the right hand side, and omitting mention of the insulation blocks, thermal conditioning section 30 begins with plate 50 and includes a thermal control assembly 61, which comprises a heater manifold 60, which includes (schematically) the oil inlet flow path 82 from worm gear chamber 46, and the oil return path 84, which runs from the heater manifold 60 back to asset 1. Heater manifold 60 includes a chamber 90 that is sized to receive sensor assembly 70, which as noted is electrically connected to circuit board 62 with flex circuit 72 and which is retained in the chamber with a bracket 71. Heater manifold 60 is a block of metal such as aluminum that is heated by a pair of resistive heating elements 92 (only one of which is shown in the perspective view of FIG. 7) that are mounted to first heater board 74 and which are received in openings or slots 94 in heater manifold 60. Openings 94 are located on either side of chamber 90 and include at their inner end thermal pads onto which the resistive heating elements that are pressed in the assembled unit, but which are not visible in the perspective views of the drawings. The slots 94 are arranged on either sides of the location in manifold 60 where sensor 70 resides in the manifold so that the heating elements are arranged in close proximity to the sensor 70 in the manifold 60. A temperature sensor 95 is provided on manifold 60 between the two slots 94. Oil inlet flow path 82 and oil return flow path 84 both open into chamber 90, the inlet flow path defining the delivery path for aliquots of oil flowing into the sensor assembly 70 within chamber 90 and the oil flow return path 84 defining the flow path for aliquots of oil flowing from the sensor assembly and ultimately back to asset 1.

Figure 8:
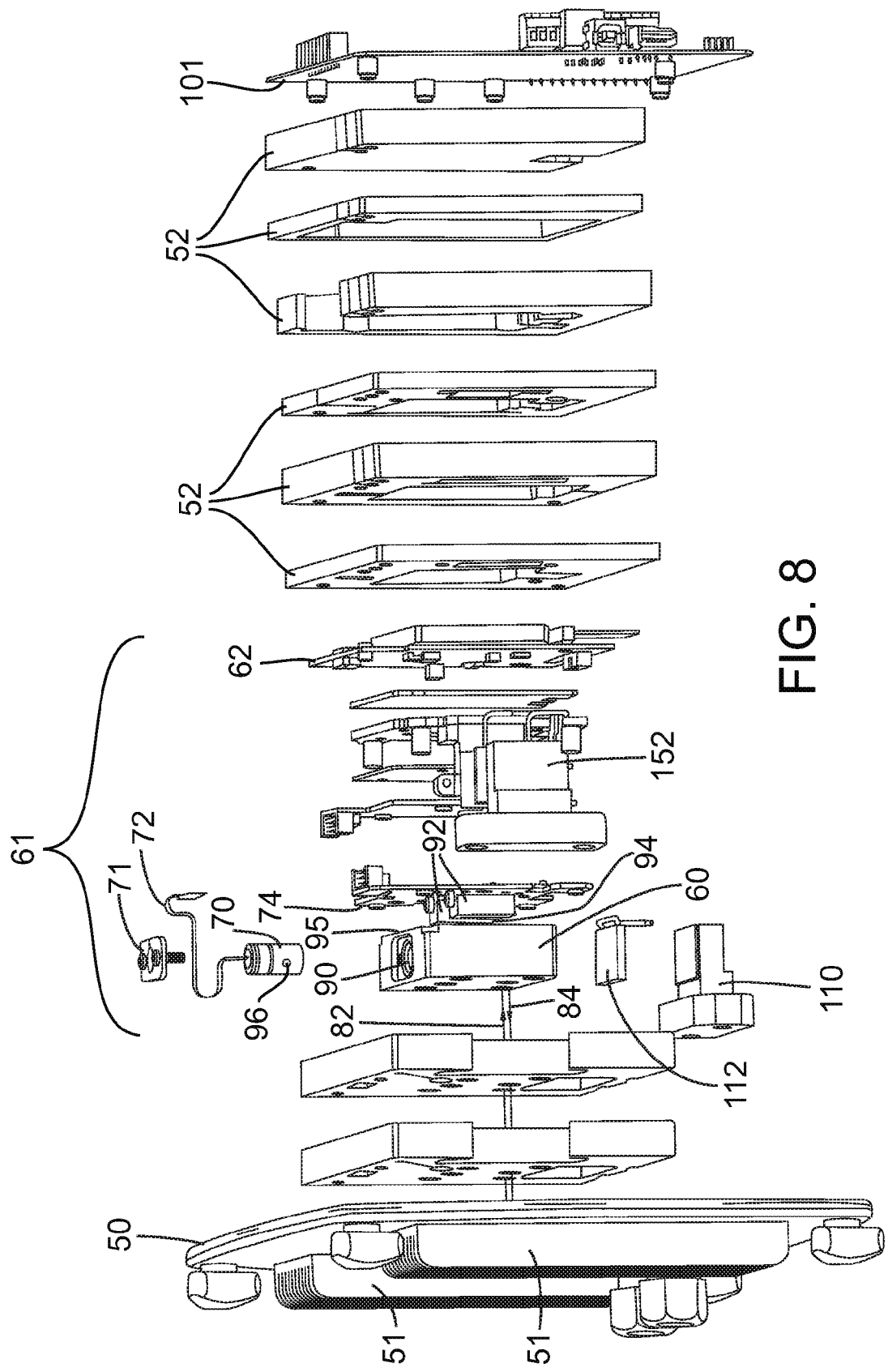
FIG. 8 is yet another perspective and exploded view of selected components of the thermal conditioning section apparatus shown in FIG. 3.

Sensor assembly 70 includes ports 96 (one of which is shown in FIG. 8) that define oil flow paths through which oil enters and escapes the sensor assembly. The solid state circuitry that defines the gas detection functionality of the sensor assembly are contained within the assembly 70.

Figure 8A:
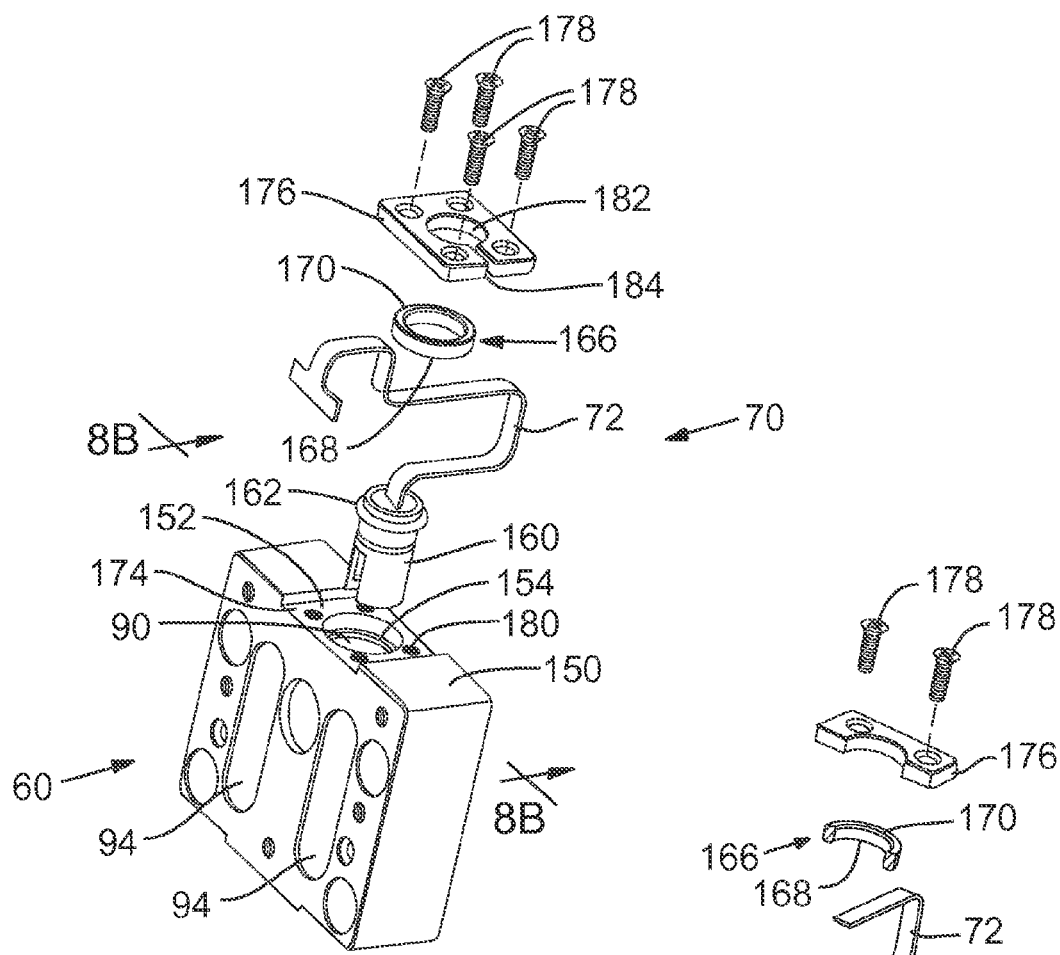
FIG. 8A is a perspective and exploded view of an alternative embodiment of the assembled heater manifold and sensor assembly that incorporates a sealing system.
Figure 8B:
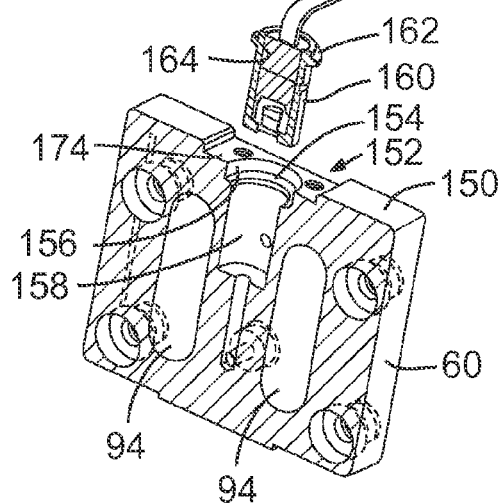

As noted above, it is important to insure that all connections and fittings are sealed so that there are no leaks in the system and apparatus 10. Any leaking oil will result in erroneous data. One of the most critical locations for a leak-free and fluid-tight environment is in heater manifold 60 and with sensor assembly 70 that resides in chamber 90 in the manifold. With reference to FIGS. 8A through 8D, a sealing apparatus is detailed that provides a completely leak-free environment for the manifold 60 and the sensor assembly 70. With reference first to FIGS. 8A and 8B, the heater manifold 60 and sensor assembly 70 are shown in isolation in a perspective and exploded view. The upper surface 150 of heater manifold 60 has a recessed area 152 that surrounds the opening into chamber 90. An annular ledge 154 is formed in chamber 90 so that there is an upper chamber portion 156 that has a greater diameter than a lower chamber portion 158. The sensor assembly 70 includes a sensor housing 160 that has an O-ring 162 in an O-ring groove 164 near the "upper" end of the sensor housing 160. It will be appreciated that the electronic circuitry that defines the sensor portion of sensor assembly 70 is retained within the sensor housing 160 and that oil flows into and out of the housing to expose the electronic circuitry to the oil, as detailed elsewhere.

When sensor assembly 70 is inserted into chamber 90—i.e., with the sensor housing 160 inserted into the chamber—the O-ring 162 rests on ledge 154, as best seen in FIG. 8D. A clamp ring 166 has an outer diameter that is slightly less than the inner diameter of chamber 90 at upper chamber portion 156 and an inner diameter that allows the clamp ring to slide over the upper portion of the sensor housing 160. Stated another way, with the sensor assembly 70 inserted into chamber 90, clamp ring 166 is inserted into upper chamber portion 156 such that the inner edge 168 of the clamp ring bears against O-ring 162 and such that the outer edge 170 of the clamp ring is above the level of surface 174 of the recessed area 152.

With the clamp ring 166 thus assembled with heater manifold 60 and sensor assembly 70, a retaining plate 176 which is sized to fit into recessed area 152 is attached to the heater manifold 60 with four screws 178, which thread into threaded openings 180 in the heater manifold. The retaining plate 176 includes a central opening 182 that is smaller in diameter than clamp ring 166 but larger in diameter than the uppermost end of sensor housing 160. The retaining plate also has a slot 184 through which flex circuit 72 may be inserted. The retaining plate therefore makes contact with the clamp ring but not the sensor housing. Since the outer edge 170 of the clamp ring 166 is above the level of surface 174, as the screws 178 are tightened the retaining plate 176 is drawn toward the heater manifold in recessed area 152. As this happens, the retaining plate pushes the clamp ring downwardly, heater manifold 60 to thereby compress the inner edge 168 of the clamp ring against the O-ring 166, which as noted above rests on ledge 154.

The compression of the O-ring 162 between the ring clamp 166 and the ledge 154 defines a completely leak-free connection between the sensor assembly 70 and the heater manifold 60.

Figure 9:
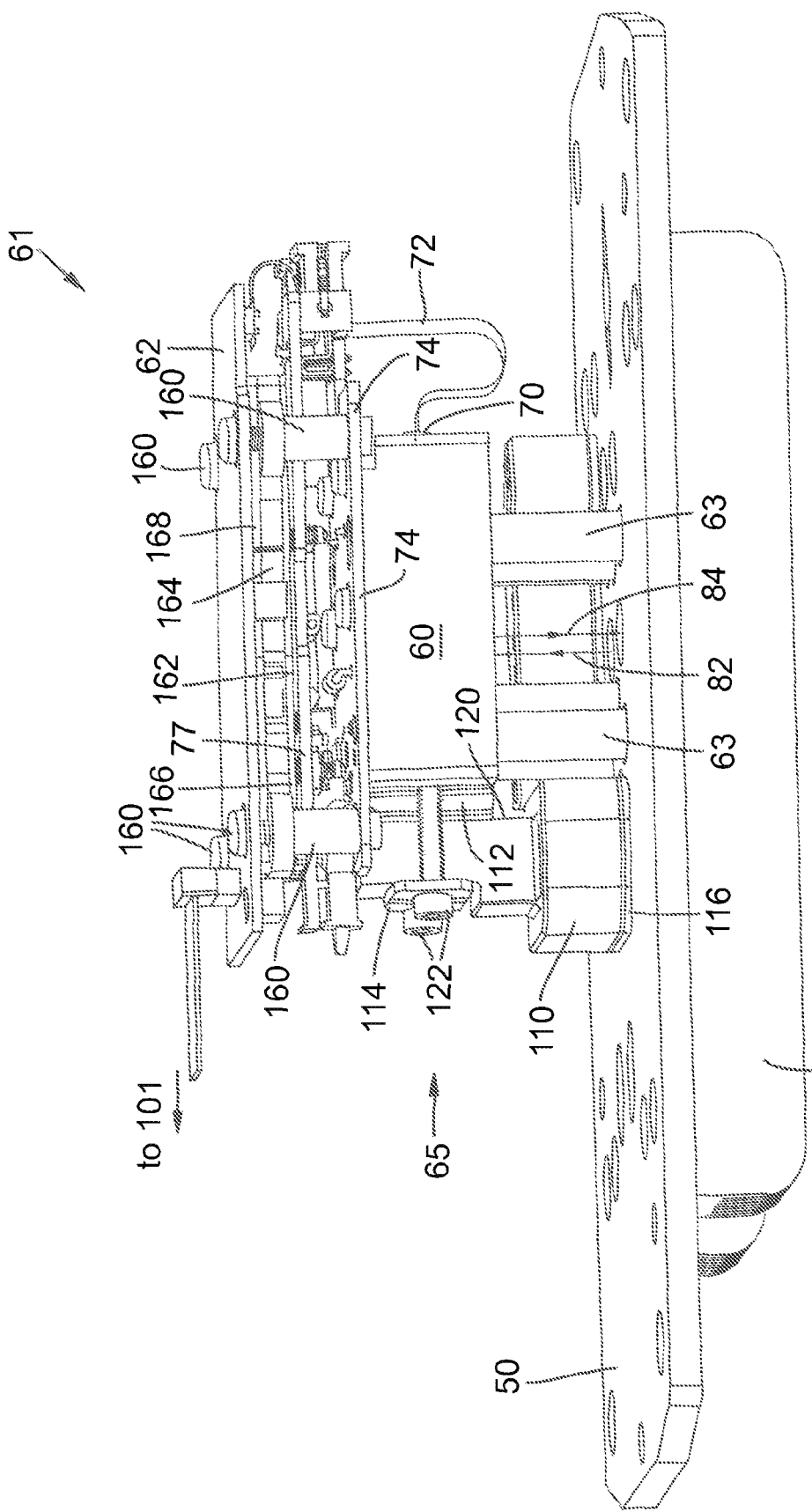
FIG. 9 is a perspective and relatively greater close up view of the thermal control assembly according to the present invention, showing the components of the assembly in an assembled condition.
Figure 10:
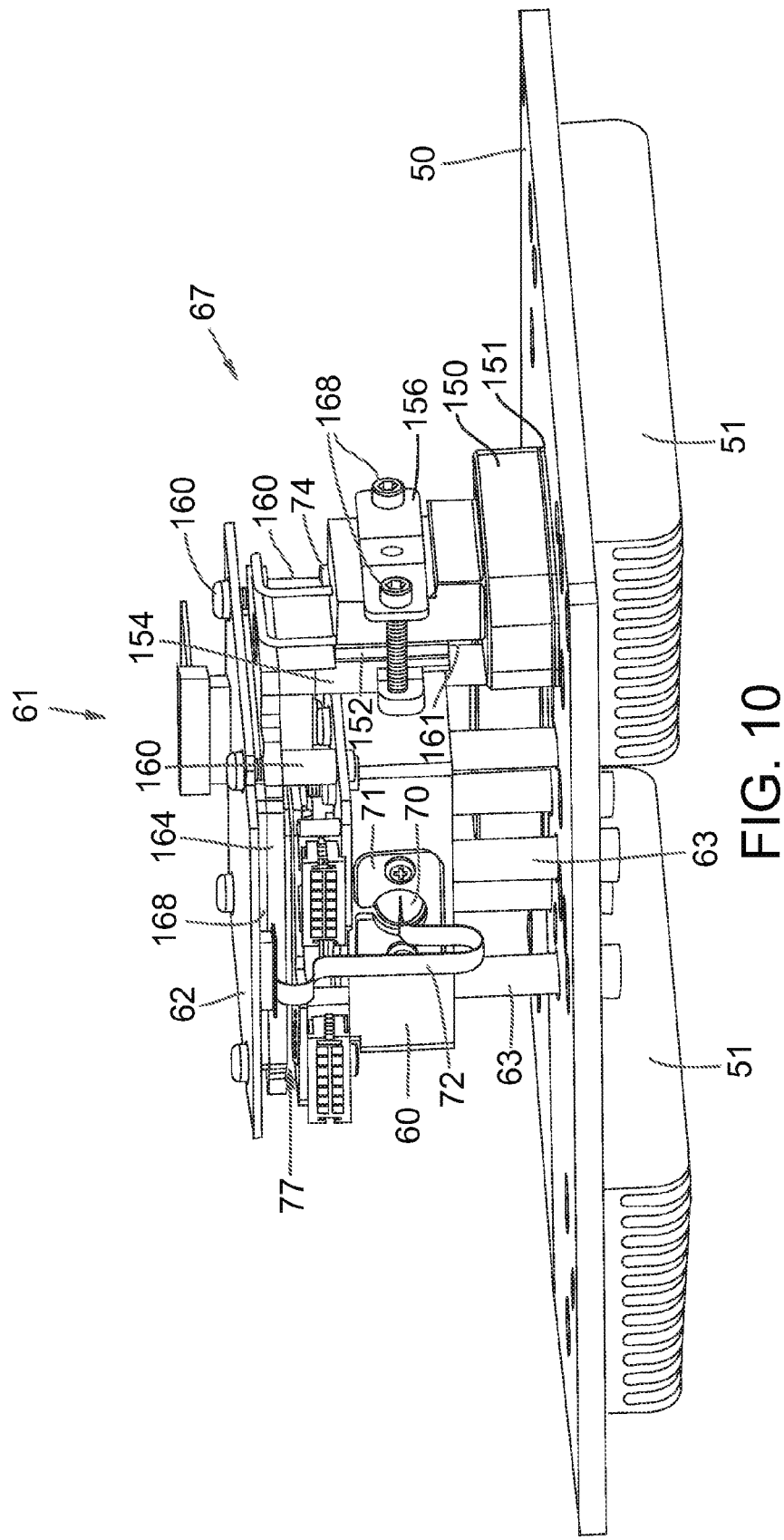
FIG. 10 is a perspective view similar to FIG. 9 of the thermal control assembly but showing the assembly from a different point of view from the view of FIG. 9.

In FIGS. 9 and 10 the thermal control system 61 is shown in isolation and in an assembled condition with all insulating blocks 52 removed in order to show the orientation of the various components. Beginning with FIG. 9, the components of thermal control system 61 are attached directly to the side of plate 50 that faces the thermal conditioning section 30—that is, the side of plate 50 opposite heat sinks 51. As noted, thermal control system 61 comprises first and second thermal zones 65 and 67. The first thermal control zone 65 is configured for heating and/or cooling the sensor 70 by heating and cooling manifold 60 into which the sensor 70 is retained, and will be described first.

First thermal zone 65 comprises generally the following essential components:
  Heater manifold 60;
  heat transfer block 110;
  first heater board 74; and
  TEC 112.

Heater manifold 60 is mounted to plate 50 on plural stand-offs 63 that mount the manifold in a spaced apart relationship with the plate 50, as shown. The oil inlet path 82 into manifold 60 and the oil outlet path 84 are shown schematically. Heat transfer block 110 is mounted to plate 50 with a thermal pad 116 between the mounting surface of the transfer block 110 and the plate. The heat transfer block is preferably a relatively massive structure fabricated from a metal such as aluminum that has excellent thermal transfer qualities. A first facing surface of TEC 112 is mounted to the inner-facing surface 120 of heat transfer block 110 that faces toward manifold 60; the opposite surface of TEC 112 abuts and is directly attached to manifold 60. A TEC strap 114 extends across heat transfer block 110 and screws 122 extend through the strap 114 and thread into threaded bores in manifold 60. When screws 122 are tightened, TEC 112 is tightly sandwiched between the heat transfer block 110 on one side, and the manifold 60 on the opposite side of the TEC 112. More specifically, the first facing surface of TEC 112 is pressed against heat transfer block 110 and the opposite facing surface is pressed against manifold 60. In addition to use of strap 114, or as an alternative to the strap, an adhesive having good thermal transfer qualities may be used to bond these sandwiched parts together. The abutting relationship and close association of the TEC between the manifold and the heat transfer block insures excellent heat transfer between these components. TEC 112 is electrically connected to second heater board 77 and is controlled by the electronic control systems associated therewith.

The nominally "cold" side of TEC 112 faces and abuts manifold 60 and the nominally "hot" side of TEC 112 faces and abuts heat transfer block 110. As noted, however, since TEC 112 is a Peltier device the direction of heat transfer may be reversed by reversing polarity of the current through the TEC.

First heater board 74 is mounted directly to manifold 60 so that the two resistive heating elements 92 are held in slots 94 with the heating elements pressing against the pads contained in the slots.

Stand offs 160 are arranged at roughly the four corners of first heater board 74 and support in a spaced apart relationship from first heater board 74 a metal plate 164. Mounted below metal plate 164 and in an abutting relationship thereto is a thermal pad 166. Below thermal pad 166 and spaced apart between both the thermal pad 166 and first heater board 74 is second heater board 77. A second thermal pad 168 is attached directly to the outer-facing surface of metal plate 164 and the analog sensor board 62 is mounted to the second thermal pad 168.

The second thermal zone, shown generally at 67 in FIG. 10 is configured for heating and/or cooling the analog electronics that control sensor 70, and specifically, the analog electronics associated with analog sensor board 62. The second thermal zone 67 is independently operated from the first thermal zone 65 described above and is thermally isolated therefrom.

Second thermal zone 67 comprises generally the following components:
  heat transfer block 150;
  TEC 152;
  TEC heat transfer bracket 154;

Heat transfer block 150 is mounted to plate 50 with a thermal pad 151 therebetween. As with heat transfer block 110 the heat transfer block 150 is preferably a relatively massive metal such as aluminum that has excellent thermal transfer qualities. One facing surface of TEC 152 is mounted to the surface 161 of heat transfer block 150 that faces toward manifold 60; however, the TEC 152 is not in contact with the manifold 60 and is spaced apart therefrom. TEC heat transfer bracket 154 is a metallic, roughly L-shaped member that is mounted to the opposite facing surface of TEC 152. TEC heat transfer bracket 154 is in turn attached to metal plate 158, which lies between thermal pads 164 and 166. A TEC strap 156 extends across heat transfer block 150 and screws 168 extend through the strap and thread into bores in TEC heat transfer bracket 154. When screws 168 are tightened, TEC 152 is tightly sandwiched between heat transfer block 150 and TEC heat transfer bracket 154 with a major surface of the bracket 154 pressed against the TEC 152. As above; an adhesive with good thermal transfer qualities may be used to bond these sandwiched parts together, either in combination with strap 156 or as an alternate thereto. The close association of the TEC 152 with the heat transfer block and the heat transfer bracket insures excellent heat transfer between the components and into metal plate 164. TEC 152 is electrically connected to second heater board 77 and is controlled by the electronic control systems associated therewith.

The nominally "cold" side of TEC 152 faces and abuts TEC heat transfer bracket 154 and the nominally "hot" side of TEC 152 faces and abuts heat transfer block 150, but again, the direction of heat transfer through the TEC may be reversed by reversing polarity of the current. It will be appreciated that since both TEC 112 and 152 are capable of both heating and cooling depending upon the direction of polarity of the applied current, these components are best referred to in a general sense as thermal conditioning modules. Moreover, use of the resistive heating elements 92 may be considered optional given the ability of the TECs to heat and cool. Stated another way, depending upon specific environmental conditions the resistive heating elements 92 may be omitted altogether, or alternately, not utilized by control (i.e., not powered) by control system 100.

Figure 11:
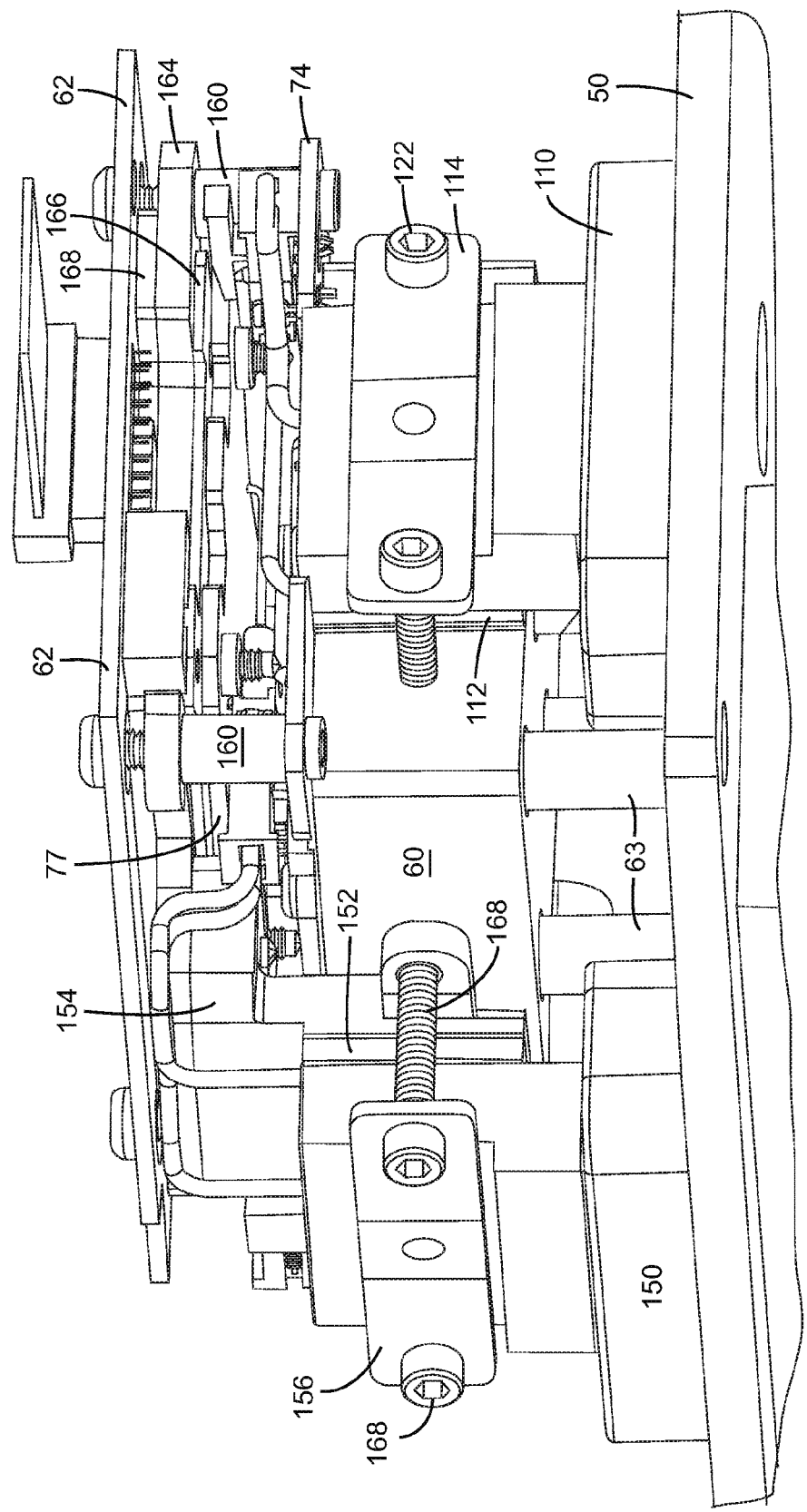
FIG. 11 is a perspective and close up view of selected components of the thermal control assembly.
Figure 12:
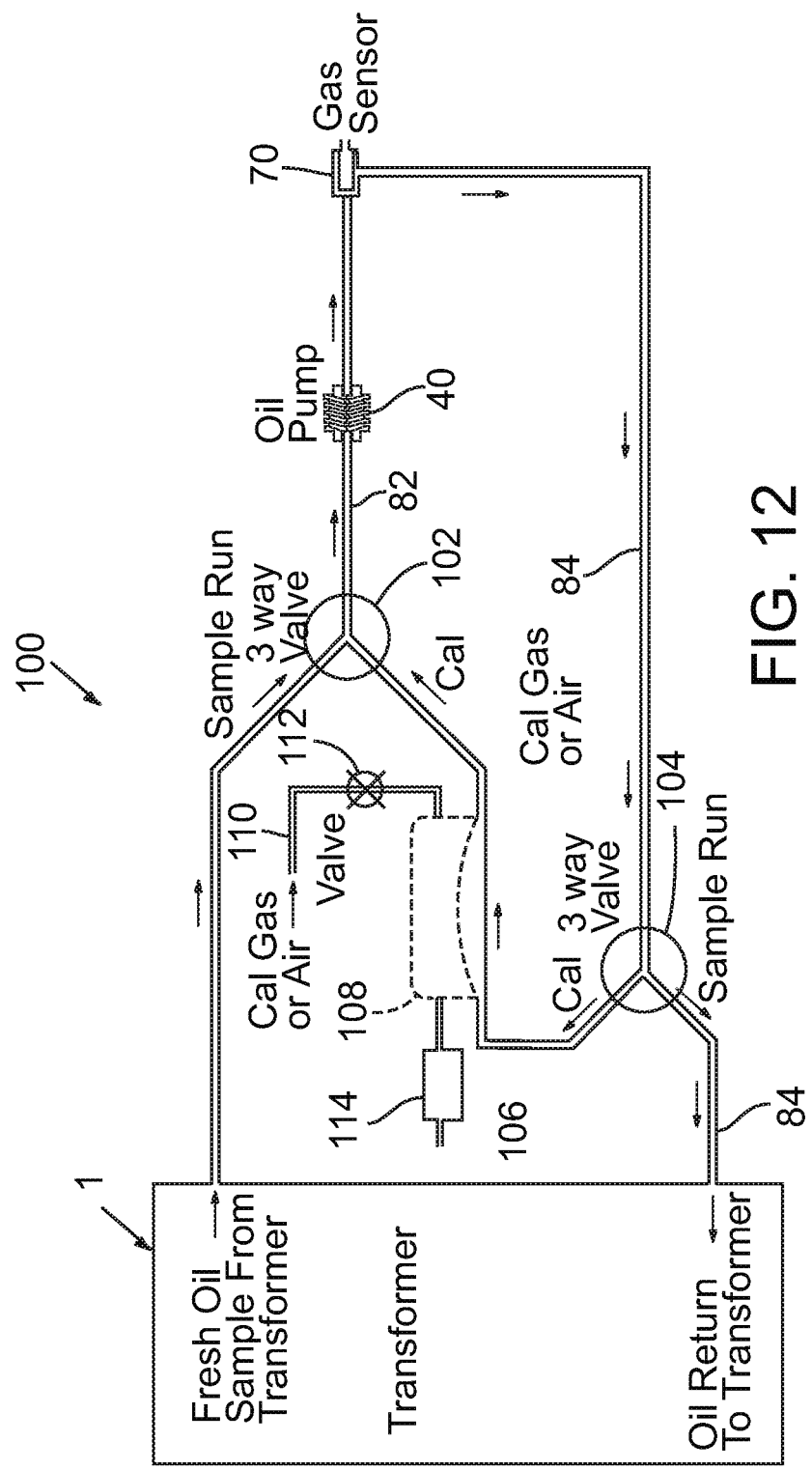
FIG. 12 is a schematic fluid flow diagram showing the fluid flow paths during an optional calibration step.

FIG. 11 is a relatively close-up view that illustrates the structural associations of selected components described above.

The entire apparatus and system 10 are under the control of a control system 100, shown schematically in FIG. 1, and which preferably includes telephony and networking capabilities. Each of the circuit boards in apparatus 10 comprises a component of the control system 100. As noted above, the control system 100 comprises firmware and electronics on four separate printed circuit boards: first heater board 74; second heater board 77; analog sensor board 62; and main control board 101; each of the boards 74. 77 and 62 are under the control of the main control board 101.

Operation

As noted, operation of apparatus and system 10 is under the control of control system 100.

Worm gear assembly 40 defines a metering pump that is capable of causing flow of precise volumes of oil from the reservoir defined by asset 1 and through apparatus 10. Initially, stepper motor 28 is operated to drive the worm gears 42 and 44 of worm gear assembly 40 to draw a quantity of oil into the cooling chamber defined by tube 80, which as noted above is part of heat sink 18, from the asset 1. Typically, the oil at this point has a relatively elevated temperature—it is thus referred to as being "hot." The hot oil resides in the cooling chamber of tube 80 for a period of time sufficient for the oil to cool, via the ambient air around heat sink 18. Apparatus and system 10 includes appropriate temperature sensing capabilities, such as thermocouples and the like connected to control system 100.

The stepper motor 28 is then operated to cause the sample of cooled oil to flow into the thermal conditioning section 30, and more specifically, through oil inlet flow path 82 into chamber 90 of heater manifold 60, and thus into ports 96 of sensor assembly 70. Stepper motor 28 is deactivated so that all oil flow in apparatus 10 ceases. The resistive heating elements 92 are powered and the heater manifold is thus heated. Heating of heater manifold 60 continues and the oil is thus heated in chamber 90. The oil is allowed to reside in chamber 90 until the oil has reached the pre-determined steady state oven temperature as determined by temperature sensor 95. The gas sensor assembly 70 is then read by control system 100 in a steady state temperature, with the oil stagnate and not flowing over or through the sensor assembly 70, which creates a much more stable environment in which the sensor assembly may determine the concentration of dissolved gas.

Once the analysis is complete, stepper motor 28 may be again activated to cause the aliquot from chamber 90 to flow through oil return flow path 84 and ultimately return to asset 1.

Analytical data from sensor assembly 70 is analyzed by appropriate techniques by control system 100, either locally or remotely, and the data are monitored.

It will be appreciated that the foregoing description of the operation contemplates a "stop flow" operation where analysis is undertaken in a zero fluid flow condition. The apparatus 10 is just as amenable to performing analysis with equal precision, reliability and control under low flow operating conditions. In a low flow analysis scheme, thermal control systems can achieve thermal control of the sample under low flow conditions where the thermal characteristics of the oil can be adequately manipulated by the pulse width modulation control. Control of the rate of flow is necessary, as if the flow is too high, thermal control can be lost. However, in that case it is only necessary that a fresh and representative sample of fluid be delivered to the sensor.

Calibration

As noted previously, the apparatus and system 10 has a capability for calibration. With reference now to FIG. 8, a calibration routine 100 is shown to include an inlet flow path 92 and return flow path 84. As shown in calibration routine 100 the fluid flow paths 82 and 84 can be optionally split so that there are two possible sample supplies separated through a pair 3-way valves, 102 in the inlet flow path 82, and 104 in the outlet flow path 84.

In a first state condition, referred to as the analysis state, the inlet and outlet fluid flow paths 82 and 84 are as described above. Thus, three way valves 102 and 104, which are under control of control system 100, are set so fluid flows through from asset 1 through valve 102 through worm gear drive assembly 40, to sensor assembly 70, as detailed above. In the analysis state, oil from sensor assembly 70 flows through flow path 84 and valve 104 back to asset 1.

In the second state condition, called the calibration state, valve 104 is operated to divert the flow of oil from flow path 84 to a calibration flow path 106, which flows through a calibration module 108. Calibration module 108 includes a semi-permeable membrane that is exposed to air or calibration gas on one side, and to the oil on the opposite side. The membrane is permeable to gas but not oil. In the calibration state, oil flows into the calibration module and then the worm gear drive assembly is stopped so that oil in the calibration module is allowed to equilibrate across the semi-permeable membrane with the reference gas—i.e., either air or a calibration gas.

In this instance, since the calibration cycle is relatively long the apparatus 10 may be routinely doing analyses while the trapped oil sample equilibrates with the calibration gas. When calibration is called for, the valves would be switched and the calibration gas inoculated oil would be introduced into the sensor region of the device. This calibration scheme would require the stopped flow operation.

A calibration loop 100 isolates the calibration gas from the fluid flow pathways 82 and 84. Specifically, a valve upstream of the calibration module (under the control of control system 100) is plumbed in the calibration gas line, which connects to the calibration module 108. A vacuum pump 114 is connected to the gas side of the membrane in module 108 and is operable to move calibration gas (including air, if air is being used as the calibration gas) into and out of the module 108. The calibration gas is flushed to atmosphere, and this avoids returning any fault gasses back to the asset 1. Thus, a calibration gas or air is drawn into the calibration module 108 on the gas side of the membrane by opening valve 112 and operation of pump 114. The oil is held in the calibration module 108 until equilibrium occurs by equilibration/inoculation of the gas from the gas side of the membrane with the oil on the oil side of the membrane. Valve 102 is then operated so that the equilibrated oil flows from calibration module 108 through flow path 106, through valve 102 and back to sensor assembly 70. When the equilibrated oil is resident in sensor assembly 70, the gas is sampled by the sensor element and the apparatus 10 is the calibrated.

Excess equilibrated/inoculated oil is flushed back to the asset 1 with fresh oil from the utility asset replenishing the secondary calibration path 106 for isolated inoculation. As noted, the gas on the gas side of the membrane on the secondary sample path could also be atmospheric air, which would effectively generate a "zero" gas standard devoid of the gas of interest.

Once calibration is done, valves 102 and 104 are returned to the analysis state operations. Calibration is conducted at regular intervals, or as necessary.

In view of the many possible embodiments to which the principles of our invention may be applied, it should be recognized that the detailed embodiments are illustrative only and should not be taken as limiting the scope of the invention. Rather, we claim as our invention all such embodiments as may come within the scope and spirit of the claims of the invention and equivalents thereto.

The invention claimed is:

1. Sealing apparatus for creating a leak-free environment for a gas sensor used for analysis of insulating oil from electrical assets, comprising:
    a manifold having a cylindrical chamber formed therein for receiving a gas sensor, said chamber having an upper portion having a first diameter and a lower portion with a second diameter that is less than the first diameter and an inwardly projecting annular ledge between the upper and lower portions;
    a gas sensor having a cylindrical sensor body, said sensor body inserted into the chamber;
    an O-ring on the sensor body, said O-ring having an outer diameter that is greater than the second diameter and less than the first diameter so that when said O-ring is inserted into the chamber the O-ring contacts the annular ledge;
    a clamp ring having an outer diameter that is less than the first diameter, said clamp ring encircling the sensor body and inserted into the upper portion of the chamber such that a lower edge of said clamp ring contacts the O-ring;
    a retaining plate attached to the manifold and in contact with the clamp ring, said retaining plate compressed against said clamp ring to thereby compress the O-ring.

2. The sealing apparatus according to claim 1 wherein the retaining plate has a cylindrical opening with a diameter greater than the diameter of the sensor body and less than the outer diameter of the clamp ring.

3. The sealing apparatus according to claim 2 wherein an upper portion of the sensor body is received in the retaining plate cylindrical opening when the retaining plate is attached to the manifold.

4. The sealing apparatus according to claim 3 wherein the retaining plate is in contact with the clamp ring when the retaining plate is attached to the manifold.

5. The sealing apparatus according to claim 4 wherein the O-ring is compressed between the annular ledge and the clamp ring when the retaining plate is attached to the manifold.

6. The sealing apparatus according to claim 2 wherein the retaining plate has a slot formed therein extending from the cylindrical opening to an edge of the retaining plate.

7. The sealing apparatus according to claim 1 wherein the sensor body has an upper surface and the manifold has an upper surface surrounding the chamber, and wherein in a first uncompressed condition the upper surface of the sensor body is positioned above the upper surface of the manifold surrounding the chamber.

8. The sealing apparatus according to claim 7 wherein the manifold further defines a recessed seat, and wherein in a second compressed condition the retaining plate is received in the recessed seat.

9. The sealing apparatus according to claim 8 including at least one heating element for heating the manifold.

* * * * *